(12) United States Patent
Farrell et al.

(10) Patent No.: US 9,427,078 B2
(45) Date of Patent: Aug. 30, 2016

(54) PERSONAL CARE PRODUCTS AND METHODS

(71) Applicant: Braun GMBH, Kronberg (DE)

(72) Inventors: Mark Edward Farrell, Medfield, MA (US); Alexander Timothy Chenvainu, Mahwah, NJ (US); Marc Philip Ortins, Reading, MA (US); Vadim Denishenko, Newton, MA (US); Jose Tadeo Vergara de Castro, Newton Center, MA (US); Hans Rolf Trawinski, Weiterstadt (DE); Alexander Hilscher, Oberusel (DE); Bert Schrempel, Hanau (DE); Martin Stratmann, Bad Soden (DE); Paul Albert Sagel, Maineville, OH (US); Phillip Maurice Braun, Exeter, RI (US)

(73) Assignee: Braun GmbH, Kronberg (DE)

( * ) Notice: Subject to any disclaimer, the term of this patent is extended or adjusted under 35 U.S.C. 154(b) by 32 days.

(21) Appl. No.: 14/048,471

(22) Filed: Oct. 8, 2013

(65) Prior Publication Data

US 2014/0096331 A1    Apr. 10, 2014

Related U.S. Application Data

(63) Continuation of application No. 11/983,287, filed on Nov. 8, 2007, now abandoned.

(60) Provisional application No. 60/589,226, filed on Nov. 15, 2006, provisional application No. 60/920,698, filed on Mar. 29, 2007.

(51) Int. Cl.
*A61C 17/22*    (2006.01)
*A46B 15/00*    (2006.01)
(Continued)

(52) U.S. Cl.
CPC .............. *A46B 15/00* (2013.01); *A46B 7/04* (2013.01); *A46B 13/02* (2013.01);
(Continued)

(58) Field of Classification Search
CPC .......... A46B 15/0002; A46B 15/0006; A46B 15/0008; A46B 15/0012; A46B 15/004; A46B 15/0044; A46B 15/0055
USPC .................................... 15/21.1–28
See application file for complete search history.

(56) References Cited

U.S. PATENT DOCUMENTS 5,561,881 A    10/1996    Klinger et al.
5,864,288 A    1/1999    Hogan
(Continued)

FOREIGN PATENT DOCUMENTS

DE    195 06 129 A1    8/1996
JP    09-168428 A    6/1997
(Continued)

OTHER PUBLICATIONS

PCT International Search Report dated Aug. 27, 2008.
(Continued)

*Primary Examiner* — Laura C Guidotti
(74) *Attorney, Agent, or Firm* — Alexandra S. Anoff

(57) ABSTRACT

In one embodiment, an oral-care system is provided. The oral-care system includes an electric toothbrush having a motor, a power source in electrical communication with the motor, and a bristle holder operatively connected to the motor. A display is in data communication with the electric toothbrush.

14 Claims, 10 Drawing Sheets

(51) Int. Cl.
*A46B 7/04* (2006.01)
*A46B 13/02* (2006.01)
*A61C 17/34* (2006.01)

(52) U.S. Cl.
CPC ...... *A46B 15/0002* (2013.01); *A46B 15/0006* (2013.01); *A46B 15/0022* (2013.01); *A46B 15/0028* (2013.01); *A46B 15/0055* (2013.01); *A46B 15/0085* (2013.01); *A46B 15/0093* (2013.01); *A61C 17/22* (2013.01); *A46B 2200/1066* (2013.01); *A61C 17/221* (2013.01); *A61C 17/3472* (2013.01)

(56) References Cited

U.S. PATENT DOCUMENTS

| | | | |
|---|---|---|---|
| 5,944,531 A * | 8/1999 | Foley et al. | 434/263 |
| 6,102,284 A | 8/2000 | Myers et al. | |
| 6,752,627 B2 | 6/2004 | Lin | |
| 6,808,298 B2 | 10/2004 | Christensen | |
| 6,902,397 B2 | 6/2005 | Farrell et al. | |
| 7,024,717 B2 | 4/2006 | Hilscher et al. | |
| 7,411,511 B2 * | 8/2008 | Kennish et al. | 340/573.1 |
| 7,748,069 B2 * | 7/2010 | Dawley | 15/22.1 |
| 8,201,295 B2 | 6/2012 | Gatzemeyer et al. | |
| 2003/0115694 A1 | 6/2003 | Pace | |
| 2005/0000044 A1 | 1/2005 | Hilscher et al. | |
| 2006/0040246 A1 * | 2/2006 | Ding et al. | 434/263 |
| 2006/0096046 A1 | 5/2006 | Hilscher et al. | |
| 2007/0136964 A1 * | 6/2007 | Dawley | 15/22.1 |
| 2007/0234493 A1 | 10/2007 | Hilscher et al. | |
| 2008/0010771 A1 | 1/2008 | Hilscher et al. | |
| 2008/0022469 A1 | 1/2008 | Hilscher et al. | |
| 2008/0022470 A1 | 1/2008 | Hilscher et al. | |
| 2008/0022471 A1 | 1/2008 | Hilscher et al. | |
| 2008/0022501 A1 | 1/2008 | Hilscher et al. | |
| 2008/0022503 A1 | 1/2008 | Hilscher et al. | |
| 2008/0028549 A1 | 2/2008 | Hilscher et al. | |
| 2008/0032265 A1 | 2/2008 | Hilscher et al. | |
| 2008/0196185 A1 | 8/2008 | Gatzemeyer et al. | |
| 2009/0092955 A1 | 4/2009 | Hwang | |
| 2009/0130636 A1 | 5/2009 | Hwang | |
| 2009/0143914 A1 | 6/2009 | Cook et al. | |

FOREIGN PATENT DOCUMENTS

| | | |
|---|---|---|
| JP | 11-346833 A | 12/1999 |
| JP | 2003-534095 T | 11/2003 |

OTHER PUBLICATIONS

U.S. Appl. No. 11/983,287, filed Nov. 8, 2007, Farrell et al.
U.S. Appl. No. 13/311,661, filed Dec. 6, 2011, Farrell et al.

* cited by examiner

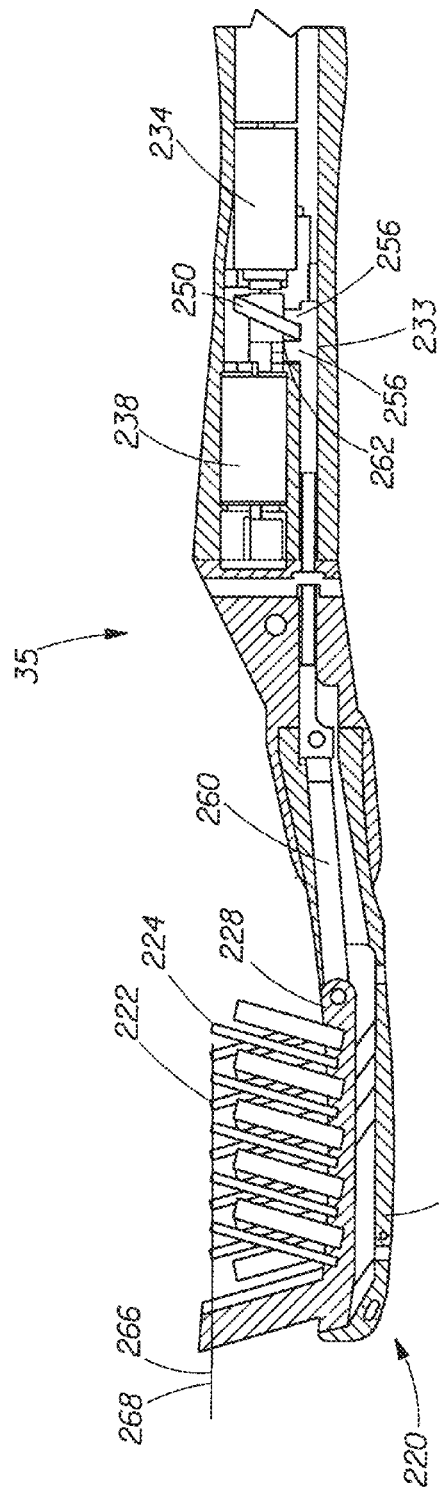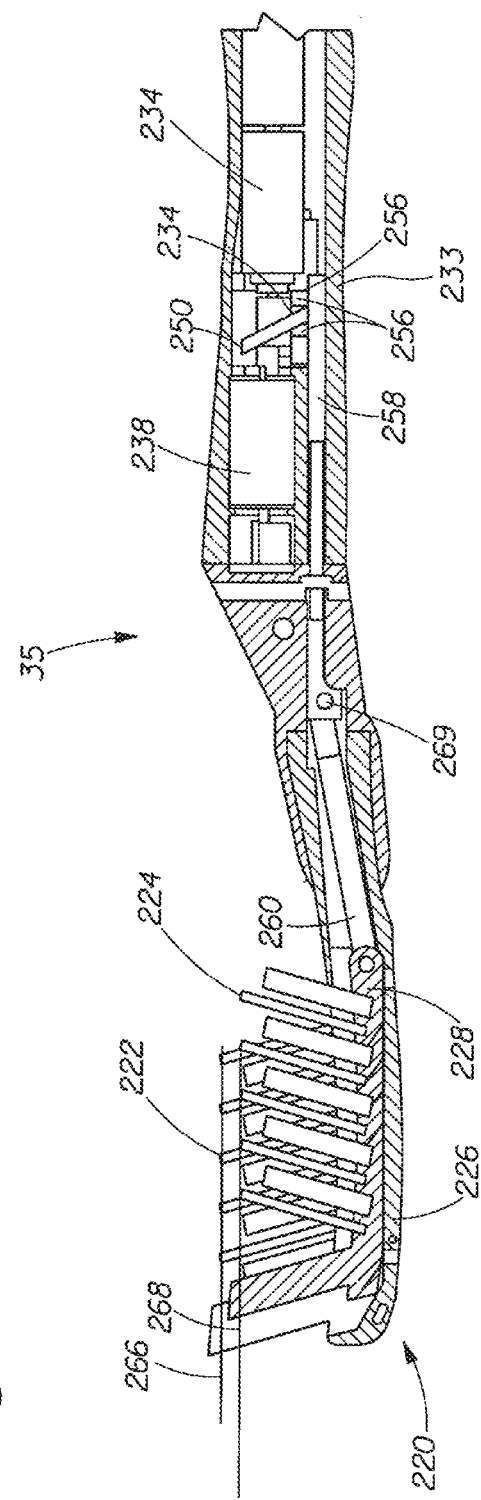

PERSONAL CARE PRODUCTS AND METHODS

FIELD OF THE INVENTION

This patent relates to personal-care products and methods, and, in one embodiment, to oral-care products and methods for use in a consumer's home.

BACKGROUND OF THE INVENTION

Consumers use numerous personal-care products in their bathrooms, where space can be very limited. There is a desire to provide products and methods for delivering useful personal care (or other) information to consumers before, during, or after use of one or more personal-care products. This information can improve the usage experience of the products, facilitate compliance in their use, provide information about the products, or provide other useful or entertaining information.

SUMMARY OF THE INVENTION

In one aspect, the invention is directed to an oral-care system comprising an electric toothbrush and a display in data communication with the electric toothbrush, wherein the display is structured to display information associated with a plurality of functional characteristics of the electric toothbrush and information associated with a plurality of characteristics of an oral-care regimen, wherein the display is separate from the electric toothbrush. In another aspect, the invention is directed to an oral-care system comprising a plurality of oral-care products and a display capable of data communication with each of the plurality of oral-care products, wherein the display is structured to display information associated with one or more functional characteristics associated with each of the plurality of oral-care products. In still another aspect, the invention is directed to a personal-care system comprising a plurality of personal-care products and a display in data communication with the plurality of personal-care products, wherein the display is structured to display information associated with at least one functional characteristic associated with at least one of the plurality of personal-care products. In another aspect, the invention is directed to a display for use with a personal-care product, wherein the display comprises a screen and at least one light source for illuminating an oral cavity and is structured to communicate data with the personal-care product. In another aspect, the invention is directed to an oral-care device for illuminating an oral cavity, comprising a mirror and at least one light source structured to emit light having a wavelength between about 400 nm and about 800 nm. In another aspect, the invention is directed to an oral-care system comprising a packaged oral-care product having an RFID tag and a display structured to communicate data with the RFID tag. In yet another aspect, the invention is directed to a kit comprising a plurality of personal-care products and a display structured to communicate data with at least some of the plurality of personal-care products. In another aspect, the invention is directed to an oral-care system comprising a display, a first oral-care product having a first data transmitter and data associated with a first reward that can be displayed on the display, and a second oral-care product having a second data transmitter and data associated with a second reward that can be displayed on the display, wherein the display is structured to communicate data with the first data transmitter and the second data transmitter. In another aspect, the invention is directed to an oral-care product comprising a package, a product for use in an oral cavity, and a data transmitter structured to transmit data associated with a reward that can be displayed on a display. In another aspect, the invention is directed to an oral-care system comprising an electric toothbrush, a data reader associated with the electric toothbrush, and at least one oral-care product comprising a data transmitter, wherein the data reader and the data transmitter are structured to communicate data. In another aspect, the invention is directed to an oral-care system comprising an electric toothbrush, at least one processor, and an interactive display in data communication with the electric toothbrush, wherein the interactive display is structured to display at least one question selectable by a user. In another aspect, the invention is directed to an oral-care system comprising at least one manual toothbrush having a data communicator and at least one display structured to communicate data with the data communicator. In another aspect, the invention is directed to an oral-care system comprising a display, at least a first oral-care product, and at least a first data transmitter associated with the at least a first oral-care product and structured to transmit data associated with at least a first reward displayable on the display, wherein the display is structured to communicate data with the at least a first data transmitter, and wherein the at least the first data transmitter is selected from the group consisting of a bar code, a magnetic device, an electromagnetic device, an optical device, and any combination thereof.

BRIEF DESCRIPTION OF THE DRAWINGS

FIG. 17 is a cross-sectional side view of the electric toothbrush of FIG. 15, wherein a bristle field is shown in a first configuration; and FIG. 18 is a cross-sectional side view of the electric toothbrush of FIG. 15, wherein a bristle field is shown in a second configuration.

DETAILED DESCRIPTION OF THE INVENTION

The following text sets forth a broad description of numerous different embodiments of the present invention. The description is to be construed as exemplary only and does not describe every possible embodiment since describing every possible embodiment would be impractical, if not impossible, and it will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). No term is intended to be essential to the present invention unless so stated. To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Figure 1:
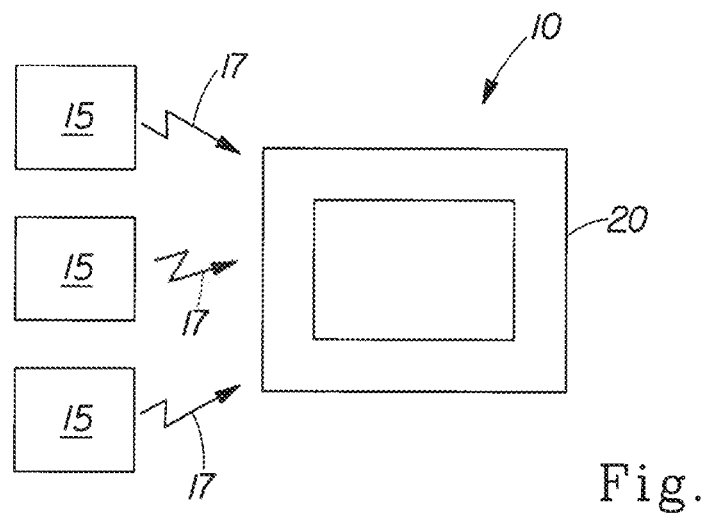
FIG. 1 is a schematic view of an embodiment of the present invention comprising a plurality of personal care systems associated with a display.

Referring to FIG. 1, in one embodiment of the present invention, a personal care system 10 comprises one or more personal-care products 15 connected by one or more data links 17 with a display 20 for displaying personal care information related to the one or more personal-care products 15. Other useful or entertaining information which may or may not be related to the personal care product 15 may also be displayed. The display 20 can be provided as a stand-alone display that can be mounted or placed upon on a variety surfaces, including hard surfaces such as a mirror or other glass surface, a countertop, a wall, shelf, or it may be mounted on, in, or placed within cabinetry or some other structure. In another embodiment, the display 20 can be provided with a projector that can project visual information onto a surface. The display 20 can be provided in a portable size and shape so that it can be taken with a user outside of the bathroom. For example, the display 20 can be provided with a belt clip so that it can be attached to a belt of a user, or the display 20 can be taken outside of the home to other locations, such as a dentist office where data stored in the display can be downloaded to a computer or other device for review by the dentist. In one embodiment the display 20 is mounted to a mirror that is adjacent one or more sinks in a bathroom. Alternatively, the display 20 can be provided as part of the personal care product. Multiple displays can also be provided, perhaps as part of both the personal care product and/or as a stand-alone display. While the display 20 can be provided as a small portable display for displaying information, in some embodiments, the display 20 can be multi-function display that may have multiple uses and receive input from sources other than the personal care system 10. Other sources can include any type of sensor, such as temperature sensors, weather or atmospheric sensors, pressure sensors, cameras, salivary sensors or other sensors that can analyze biological materials. The display might receive a television or radio signal from third party service provider (e.g., a cable company, etc.). The display 20 can be provided in a wide variety of shapes and sizes, although in one embodiment the display 20 is generally rectangular and has a length less than about 30 mm and a width less than about 15 mm. In one form, the display 20 is provided as an LCD (Liquid Crystal Display).

The one or more personal-care products 15 can be any kind of personal care product, including, but not limited to, products selected from the following product categories: oral-care products, personal grooming products (e.g., shavers or epilators), personal diagnostic products (e.g., thermometers), hair care products (e.g., shampoos, conditioners, colorants, etc.) and appliances (e.g., hair dryers, curling irons, etc.), cosmetics, toiletries, and any other personal care product. A personal care product can be any product suitable for personal use. In one embodiment, the invention is used with one or more oral-care products. The oral-care products can be selected from a variety of oral-care product sub-categories, including, but not limited to: manual toothbrushes, electric toothbrushes, rinses, dentifrices, denture care products, floss products, tooth whitening products, and any other product for use in the oral cavity. The oral-care products can be one or more products within the same sub-category and/or one or more products from a plurality of sub-categories. For example, the present invention might be used with a manual toothbrush, an electric toothbrush, a dentifrice and a rinse. In other embodiments, the invention can also be used with one or more products from other personal care product categories and/or their sub-categories. For example, the display 20 might be used with a plurality of oral-care products and a plurality of shaving products. In addition, more than one user might use the display. For example, the same display, or a plurality of displays might be used by more than one family member who uses one or more personal-care products.

The information that can be displayed is quite varied, including personal care information or other useful or entertaining information. Personal care information can be related in any manner to the one or more personal-care products, their use (including usage history or regimen information), or information concerning the user of the personal care product. Some examples of personal care information that can be displayed includes, but is not limited to, identifying information of the personal-care products (e.g., name, brand, model, logo, etc); user information;

usage instructions; information associated with the features, functions, operational parameters or status of the personal care product (collectively referred to as "functional characteristics" of the product); product usage or regimen information, and product or component replacement information. In addition, other information can be displayed, including entertainment information. For example, television broadcasts, still pictures, HTML and Internet information, calendars, and Intranet information from a home network may also be displayed. The form of the visual information that can be displayed is quite varied also and can include images, graphics, icons, text, numeric data, alpha-numeric data, graphs, charts, tables, calendars, video, etc The displayed information may be associated with one or more characteristics of the electric toothbrush 35, including, but not limited to, the speed, amplitude, or frequency of movement of a bristle holder (or toothbrush head); the pressure exerted by the toothbrush on a tooth, the status of a feature or function of the toothbrush (e.g., the toothbrush is energized or a feature of the toothbrush is activated or deactivated); the status of a power source (e.g., a battery that is fully charged, 50% charged, or needs to be recharged or replaced); the type of brush head or cleaning elements (e.g., massaging elements, polishing elements, etc.) that are coupled to the electric toothbrush, and/or the configuration of the bristle field, etc. A characteristic of a toothbrush (or any personal care product) may be any aspect concerning the features of the toothbrush, the performance of the toothbrush, or the status of the toothbrush or any of its components.

The display may also display information associated with one or more characteristics of an oral-care regimen (e.g., tooth brushing cycle), such as brushing time, recommended brushing location, usage or regimen instructions, or a reward upon completion of the brushing regimen, or a daily oral-care product reminder (e.g., a reminder to floss or use a rinse). A characteristic of an oral-care regimen may be any aspect concerning who performs the regimen, how the regimen is performed, what products are used with the regimen, when the regimen is performed, why the regimen is performed, the efficacy of the regimen, a user's perception of or satisfaction with the regimen, rewards, or other information concerning the regimen or products used with the regimen.

The display 45 can also display information that is unrelated to the characteristics of the electric toothbrush or the tooth brushing cycle/regimen, such as weather information; a joke (e.g., a new joke each day); sports information; news headlines; traffic information; stock quotes; music information where the display contains a speaker for producing music (e.g., broadcast music as well as stored music, such as an MP3 file); and marketing information, such as coupons for the purchase of oral-care products associated with the manufacturer of the electric toothbrush or recommendations concerning other oral-care products. In one embodiment, the display 45 can display information associated with a plurality of functional characteristics of the electric toothbrush 35 and information associated with a plurality of characteristics associated with the oral-care or toothbrushing regimen, although it will be appreciated that the text, graphics, images, video, icons, and audio described herein can be displayed in any combination, in whole or part, by the display 45. Other visual or audio information may be substituted or provided in any combination.

Further, in addition to images, audio can also be produced or otherwise transmitted from the display, alone or in combination with visual information, including music, sounds, audio signals, and audio associated with any video or images that are displayed. A display need not be provided with the present invention, and in some embodiments the display can be replaced by a device having speaker and no display. This audio device can, however, be mounted in the any of the same manners described herein for the display. This device can be connected by a data link to one or more personal-care products in the same manner as described herein with respect to the display 20.

While a variety of personal-care products can be used with the present invention, for ease of discussion, the invention will now be generally described hereafter with respect to one or more oral-care products, although it will be appreciated that the description and various features of the invention can be used with any personal care product or plurality of products.

Figure 2:
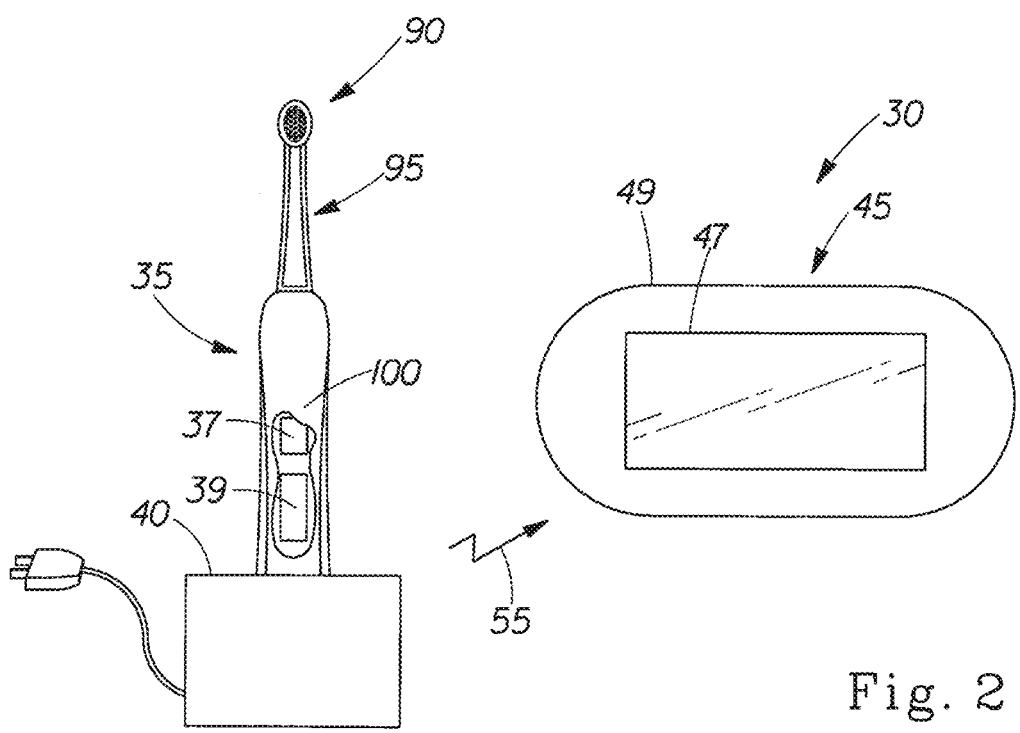
FIG. 2 is a perspective view of another embodiment of the present invention of an oral-care system associated with a display.

Referring to FIG. 2, an oral-care system 30 comprising an electric toothbrush 35, a base 40 for receiving the electric toothbrush 35, and a visual and/or audio display 45 that is in continuous and/or intermittent data communication with the electric toothbrush 35 and/or the base 40 before, during, and/or after use by a consumer of the electric toothbrush 35. A wide variety of electric toothbrushes can be used with the present invention. The electric toothbrush illustrated in FIG. 2 comprises a motor 37 and an energy source 39 that is in electrical communication with the motor 37. The motor is operatively coupled to one or more movable bristle holders 40 disposed on the head 90 to move one or more of the bristle holders. The bristles holders can rotate, oscillate, translate, vibrate, or undergo a movement that is a combination thereof. The head 90 can be provided as a removable head so that it can be removed and replaced when the bristles (or other component) of the bristle holder have deteriorated. Examples of electric toothbrushes that may be used with the present invention, including examples of drive systems for operatively coupling the motor to the bristle holders (or otherwise moving the one or more bristle holders or the head), types of cleaning elements for use on a bristle holder, structures suitable for use with removable heads, bristle holder movements, other structural components and features, and operational or functional features or characteristics of electric toothbrushes are disclosed in USPNs 2002/0129454; 2005/0000044; 2003/0101526; U.S. Pat. No. 5,577,285; U.S. Pat. No. 5,311,633; U.S. Pat. No. 5,289,604; U.S. Pat. No. 5,974,615; U.S. Pat. No. 5,930,858; U.S. Pat. No. 5,943,723; 2003/0154567; 2003/0163881; 2005/0235439; U.S. Pat. No. 6,648,641; 2005/0050658; 2005/0050659; 2005/0053895; 2005/0066459; 2004/0154112; U.S. Pat. No. 6,058,541; and 2005/008050

Figure 3:
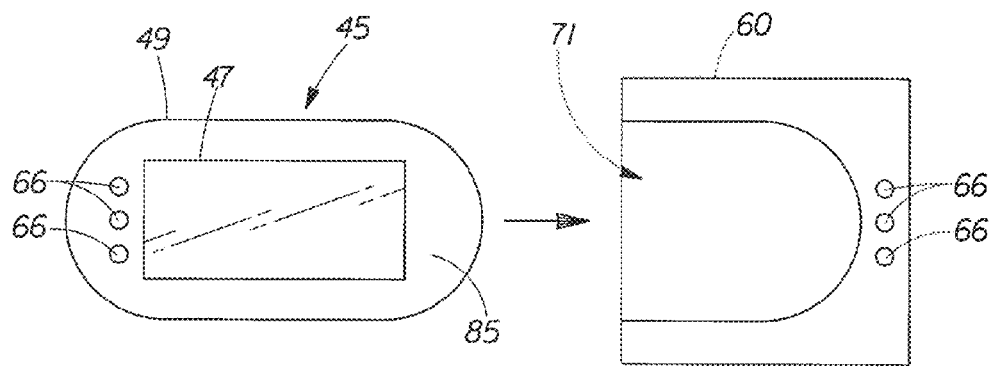
FIG. 3 is a front view the display of FIG. 2 and a mounting structure for slideably receiving the display.

The display 45 comprises a screen 47 disposed within a housing 49. The screen 47 can be provided as a liquid crystal (LC) screen. As seen in FIG. 3, the display 45 can be slideably received within a mounting structure, such as sleeve 60, for attachment to a surface. Other means of attachment are possible, including but not limited to adhesives, snap-fits, hook and loop fasteners like Velcro, etc. While the display 45 will be described hereafter as containing a screen 47 for displaying images, icons, text, graphics, or video, it is contemplated that an audio device that does not have a screen for displaying visual information can substituted as previously described. The base 40 can be used to recharge the power source, such as a battery, within the electric toothbrush 35. The base 40 can be configured to receive a plurality of electric toothbrushes, or other oral-care products such as manual toothbrushes, accessories for the electric toothbrush 45 (such as a plurality of heads or other attachments), and/or other personal-care products. The base 40 can be coupled by a power cord to an external source of power, such as an AC outlet (not shown). The oral-care system 30 can use a variety of arrangements, singly or in combination, to implement data communication between the display 45 and the electric toothbrush 35 and/or base 40. In one embodiment, the toothbrush 35 and/or the base 40 are in wireless communication with the display 45 via wireless data link 55. The wireless data link 55 may be based upon a suitable short range radio frequency communication technology, such as Bluetooth, WiFi (802.11 based or the like) or another type of radio frequency link, such as wireless USB at 2.4 GHz. For radio transmissions, an antenna can be mounted on a printed circuit board (PCB) disposed in the electric toothbrush 35, base 40, sleeve 60, and/or the display 45.

For infrared (IR) transmissions, one or more IR transmitter diodes can be mounted in the electrical toothbrush 35, the base 40, the sleeve 60, and/or the display 45. An IR wavelength suitable for use with the present invention is 950 nm modulated at 36 KHz. Other wireless data communication technologies may be used. In some embodiments, a plurality of oral-care products may be in data communication with the electric toothbrush 35, the base 40 and/or the display 45, as previously described. The data transfer can be one-way and/or two-way, continuous and/or intermittent, modulated, or any combination of the foregoing, between the display 45, the base 40, electric toothbrush 35, and/or any other personal care product. As previously described, the display 45 can be configured to communicate using one or more types (e.g., IP wireless radio, etc.) of data communication methods, and the same display 45 can employ different types of data communication methods with different personal-care products.

Figure 4:
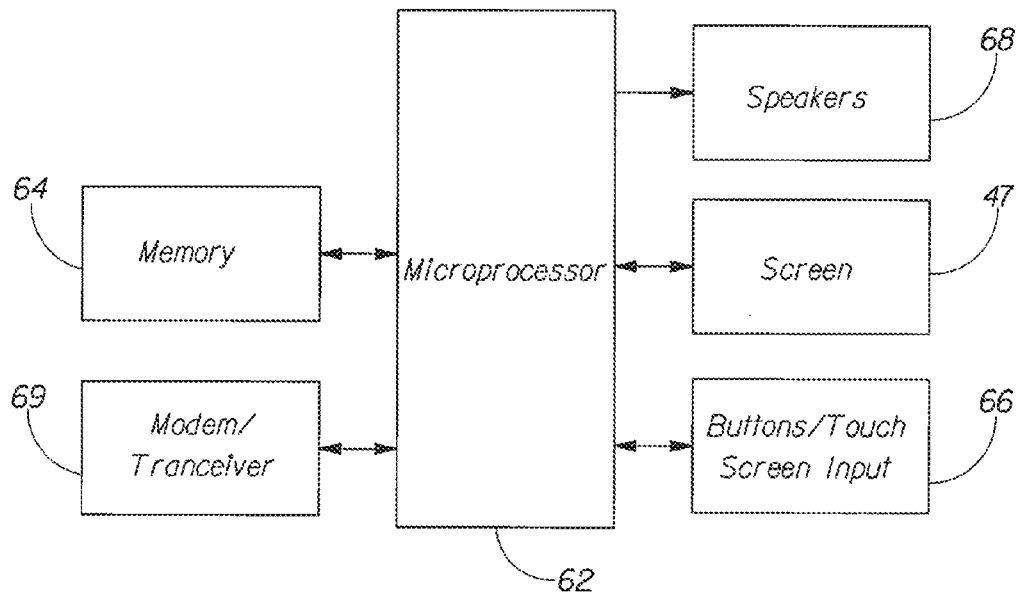
FIG. 4 is a block diagram of electrical and electronic components that can be used with the present invention.

As depicted in FIG. 4, the electric toothbrush 35, display 45, or base 40, can include a processor 62 in data communication with memory 64. The processor 62 may be a general purpose processor, an application specific processor or circuit chip, a microprocessor, or combinations of one or more of the foregoing. The memory 64 may store a variety of information, including any personal care information, entertainment information, or any other useful information, including data associated with oral-care analyses (discussed further below). The memory 64 may also contain program code or instructions that affect operation of the processing device 62. The memory may additionally contain stored or cached entertainment information, such as MP3 files, video/graphics and the like. The memory 64 may be erasable/writable non-volatile memory, such as flash memory, dynamic volatile memory, or other suitable memory including replaceable memory media, and/or combinations thereof. The processor 62 can be coupled to various user interface devices including the screen 47, buttons 66 associated with the screen 47, and/or a speaker 68 associated with screen 47. A modem, transceiver or other suitable communication device 69 can couple the processor 62 to networks, broadcast sources and the like. The various components described above can be distributed between the sleeve 60, display 45, base 40, and/or electric toothbrush 35. Alternatively, the one or more components can be combined on a single circuit board that is disposed in one of the sleeve 60, display 45, base 40, or electric toothbrush 35. The processor 62 may initiate an activity automatically as a result of use of the electric toothbrush 35. For example, removal of the toothbrush 35 from its base 40 may initiate a communication between the base 40 and the display 45 to begin displaying information associated with an oral-care activity. Alternatively, energization of the toothbrush 35, or activation of a feature thereof, may cause the display of information on the display 45. A still further alternative permits a user to select and initiate an activity or display of information via a user interface, e.g., buttons 66 or screen 47 if the screen 47 is configured as a touch screen. The oral-care system 30 could also be configured to be responsive to voice commands to select and initiate the display of information.

The processor 62 may be configured to execute a set of instructions and/or a setup application. The setup application can be used to, for example, set a clock or calendar, to couple the oral-care system 30 to a network or other source of data and the like. The setup application may furthermore allow a user to select graphic themes and images, colors, sounds, messages and the like and to define multiple different users who might interact with the oral-care system 30 or the display 45, each possibly having a unique graphic theme or images, colors, sounds, etc.

The processor 62 may also be configured to execute a set of instructions associated with one or more analyses of personal care information that is input from sensors, the users, or the personal-care products. For instance, analyses of brushing times, oral-care regimens and/or habits might be performed (e.g., determining average brushing length, day or evening brushing habits, etc).

Figure 5:
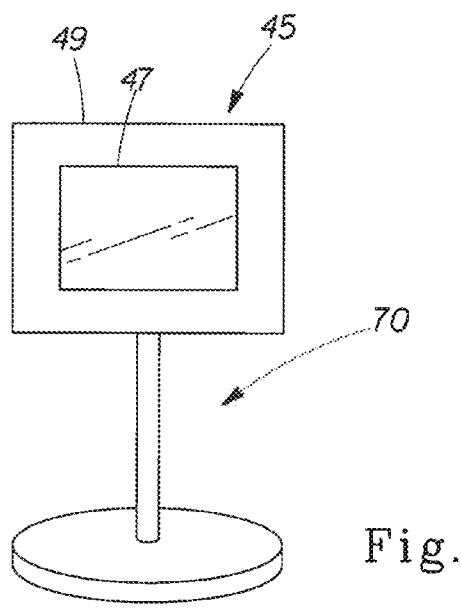
FIG. 5 is a perspective view of another embodiment of the present invention, wherein the display of FIG. 2 is provided with a stand.
Figure 6:
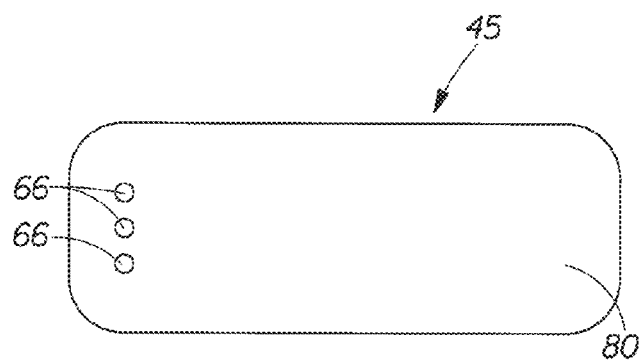
FIG. 6 is a rear view of the display of FIG. 2.

As previously discussed, the display 45 can be used with a suitable mounting structure to allow it to be mounted to a surface, such as a wall or mirror, or placed on a surface, such as a countertop. The surface may be horizontal, vertical or angled from vertical. In one embodiment, the sleeve 60 can be provided for slideably receiving the display 45, as shown for example in FIG. 3. The sleeve 60 can be mounted to the surface using adhesive, screws or any other suitable fastener known in the art. Additionally, the sleeve 60 might include a swiveling structure that is articulated to allow the display 45 and/or sleeve 60 to rotate, angle or extend toward a user. A ball and socket structure is one means that could be used to provide a swiveling motion. An alternative mounting arrangement illustrated in FIG. 5 includes an upstanding stand 70 upon which the display 45 is positioned. The display 45 may be secured to the stand 70 or may rest upon the stand without securing attachment. The stand 70 may provide for pivoting, rotating, articulating or other positioning motion to allow adjustment of the position and/or angle of the display 45 relative to the user.

Referring again to FIG. 3, the sleeve 60 has an opening 71 through which screen 47 of the display 45 can be viewed or accessed when the display 45 is received within, or attached to, the sleeve 60. The display 45 can be removed when necessary to replace one or more batteries (not shown) which can be used to power the display 45. The power source for the display 45 can be disposed within the housing 49 of a display 45. Buttons and/or switches 66 can be located on a rear surface 80 of the display 45 to control or enable one or more functions of the display 45 or to otherwise provide data input to the display 45. Alternatively, the buttons can be located on a front surface 85 of the display 45, on the sleeve 60 (which can be in electrical communication with the display 45), or the display 45 can incorporate a touch screen so that that data can be input directly using the screen. If the screen 47 is provided with touch sensitive capability, the screen 47 may display virtual buttons and selection features allowing user manipulation, control and option selection to be affected directly through the display 45. In some embodiments, data input to the display 45 or the sleeve 60 might control functions or operations of the electric toothbrush 35 (or another personal care product). For instance, a user might provide an input to the display 45 and/or the sleeve 60 that is transmitted to the base 40 and/or the electric toothbrush 35 to change the operation of the electric toothbrush 35. In other embodiments, buttons or switches 75 can be used to initially set parameters displayed by the display, such as the time and/or date for a clock or calendar that is displayed by the display 45.

In another example, a button or switch 66 might enable a night light function, wherein the screen 47, or a portion thereof, produces a low level light in the evening or overnight. The night light function might be governed by a clock or timer that is associated with the display 45, the base 40, or the electric toothbrush 35. The night light function might also be activated by detection of motion in the bathroom by a motion sensor located in the toothbrush 35, the base 40, the sleeve 60, or the display 45.

Figure 7:
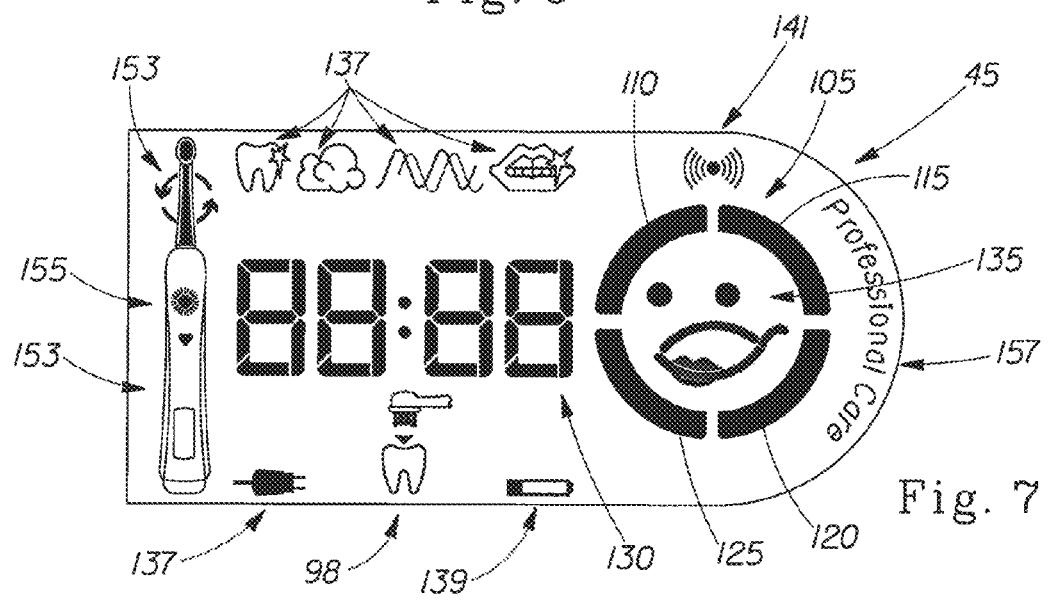
FIG. 7 is a front view of the display of FIG. 2, illustrating a variety of visual information that can be displayed by the display.

Referring to FIG. 7, in one embodiment, displayable information associated with one or more characteristics of the electric toothbrush 35 will now be described. An example of a pressure image 98 that can be displayed to signal high brushing pressure is shown in FIG. 7. A pressure sensor can be incorporated in the head 90, neck 95, or handle 100 of the electric toothbrush 35. An example of a pressure sensor suitable for use with the present invention is described in U.S. Pat. No. 7,120,960. The electric toothbrush 35 or the base 40 can transmit pressure data to the display 45. The display 45 can display the pressure data (or other oral-care or personal care information) as numeric, alphanumeric, textual, images, or graphical information. Alternatively or in combination with the visual information, an audio signal might also be generated. For instance, an audible signal might alert a user that a certain brushing pressure has been exceeded.

Information associated with one or more brushing modes can also be displayed. For example, images 137 might indicate a basic cleaning mode; a soft brushing mode; a massaging mode; and a polishing mode. The operative brushing mode can be selected by user providing an input to the electric toothbrush 35, the base 40, the display 45, or the sleeve 60 via any user input device.

The electric charge of the electric toothbrush 35 and/or the display 45 can be represented by images 137 and 139, respectively, so that a user knows when a battery may need to be replaced or when the electric toothbrush 35 needs to be recharged. An image 141 can be also provided to indicate whether the display 45 is sending or receiving data. One or more images 153 might also be used to indicate when a component of the oral-care system, such as a brush head, needs to be replaced. Data could also be displayed that indicates the amount of useful life left for a component. For instance, the display might display a percentage of the useful life that is left for a brush head (e.g., 25% or 50% might be displayed). Other images or audio that might be produced by the display 45 include indications that a particular function of the toothbrush 35 has either begun or has terminated. For example, if the toothbrush 35 includes an LED, such as described in USPNs 2005/0053896; 2005/0053895; 2005/0053898; and 2005/00550659, the display might display an image that indicates the LED is either On or OFF, or the time remaining before it either turns On or turns Off. If the toothbrush dispenses a composition, such as described in U.S. Pat. No. 6,648,641, the display can display information about whether the toothbrush is dispensing or not dispensing a composition or an identification of what composition is being dispensed. An image 153 of the oral-care product (in this case an electric toothbrush) can be provided and portions 155 of the image 153 can be animated (e.g., blink or illuminate) to indicate that a particular function of the electric toothbrush 35 is active. In one embodiment, a logo 157 associated with the electric toothbrush 35 can be displayed.

Information that can be displayed on the display 45 that is associated with one or more characteristics of the oral-care regimen will now be described. Referring again to FIG. 7, the display 45 might display visual and/or audio signals to prompt a user to change the region of the mouth that the user is brushing. The entire dentition (teeth) schematically shown in the display 45 can be visually divided in any number of suitable segments. For example, the display 45 might display an image 105 representing one, two, three, four, and so on segments of the dentition. If desired, the entire dentition may be represented as a single section, or as two segments, one representing the upper (aka maxillary) teeth and the other representing the lower (aka mandibular) teeth (not shown). In another example, shown in FIG. 7, quadrants 110, 115, 120, and 125 represent the four quadrants of the maxillary and mandibular arches of the dentition. In one embodiment, each of the quadrants may successively blink and/or change color to indicate when it is time to move onto the next quadrant. In another embodiment (not shown in the drawings), the display may show six segments, representing, for example, upper front teeth, lower front teeth, upper right-side teeth, lower right-side teeth, upper left-side teeth, and lower left-side teeth. One skilled in the art would appreciate that other similar embodiments of the display's schematic representation of the user's mouth, having any suitable number of dentition segments, may be used, all of which are contemplated by the invention. A count-up or count-down timer 130 can also be included, wherein the display 45 displays the amount of time remaining in a brushing cycle. The brushing cycle time can either be pre-programmed or set by a user by inputting the time period to a component of the oral-care system 30.

At the completion of a brushing cycle, which can be conveyed by either the expiration of a time period of the timer 130 and/or an indication that brushing of the last quadrant of the oral cavity is complete (e.g., by illumination, blinking, or a color change of the image associated with the $4^{th}$ quadrant), a reward can be automatically displayed to the user to indicate successful completion of the brushing regimen. In one embodiment, a smiling face 135 can be displayed within the brushing quadrants to indicate completion of the brushing regimen. The reward can be helpful in promoting completion of the oral-care regimen. A reward can comprise visual and/or audio information that is intended to stimulate a desire to complete a particular task or regimen, or visual and/or audio information which a user finds desirable or pleasurable to view and/or hear upon completion of a task. The reward can be used to signal the completion of a task, or the completion of a task can be signaled by other visual and/or audio information. In some embodiments, the user can select or input (e.g., via the display 45) the type of the reward (e.g., image) that is displayed or audio that might be played. The reward can be displayed in a variety of ways and may or may not be associated with the image 105. In some embodiments, the reward can be provided as data stored with a personal care product (e.g., as part of memory 64 or an RFID tag, discussed below) and may be unique between personal-care products. One personal care product might store data associated with a first reward while a second personal care product stores data associated with a second, different reward. The reward could be associated with themes, slogans, colors, logos, icons, images, or other graphic or visuals that are uniquely associated with the personal care product, its packaging, or its marketing/advertising characteristics or messages. For instance, a child's toothbrush having a handle in the shape of a race car might contain data for a visual reward associated with car racing. Data for a plurality of rewards could be associated with a single personal care product so that different rewards could be displayed with each use of the toothbrush to refresh or maintain user interest or might be selectable by a user.

Figure 8:
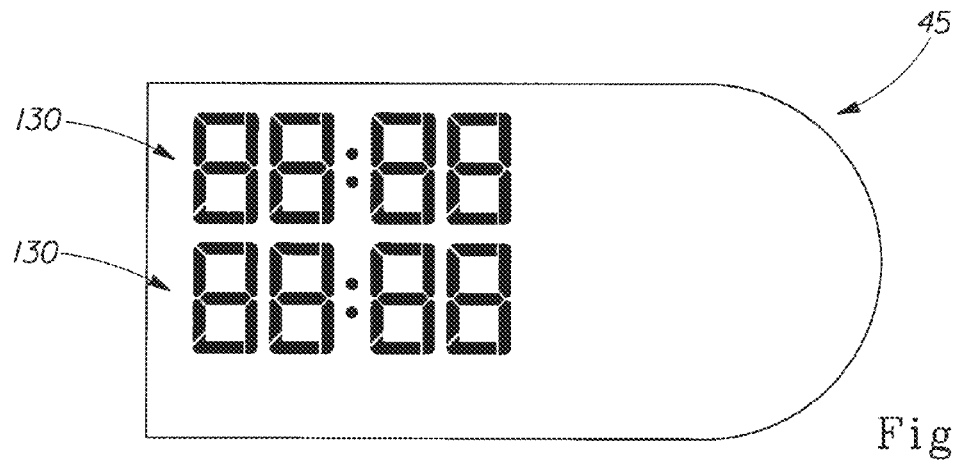
FIG. 8 is a front view of another embodiment of the display of FIG. 2, wherein a plurality of timers is illustrated.

A plurality of either count-up and/or count-down timers might be displayed on the display 45. In some embodiments, 1, 2, 3, 4, or 5 timers might be provided. For instance, one timer might display the time associated with an overall oral-care regimen (e.g., how much time out of 2 minutes remains) while a second timer might display the time associated with one or more sub-regimens or toothbrush functions within the oral-care regimen (e.g., how much time remains for a light that illuminates the oral cavity to remain on during the regimen or how much time remains for the dispensing of a composition from the toothbrush). An example of such a display is shown in FIG. 8. One or more of the timers might be directly activated by a user of the display (e.g., as by a button on the display) rather than by data transmission between the display and the electric toothbrush.

In another embodiment, the display can interactively display questions and/or information associated with one or more characteristics of an oral-care regimen. For instance, the display might display one or more questions and one or more answers that can be selected by a user via a touch screen or buttons. The questions might be displayed at the beginning, during, or at the end of one or more oral-care or brushing regimens. The functional characteristics of the electric toothbrush 35 or information concerning the oral-care regimen might be automatically changed or adjusted depending on the answers to the one or more questions. For instance, a question might ask if the brushing experience was too hard or soft. Depending on the answer, the speed, frequency, or pressure sensor limit value (i.e., the value at which a warning is displayed that too much pressure has been applied) of the electric toothbrush might be automatically adjusted, or the amount of time displayed for the timer might be adjusted. The processor 62 could implement these changes in response to the input from the user. In another instance, the display might display information concerning alternate products or instructions concerning the use of the electric toothbrush 35 (or its accessories) that might provide an improved brushing experience. In another instance, the answer to one question might lead to a second question. For example, a question might ask whether the user was pleased with the brushing experience. An answer of "no" might lead to one or more follow up questions, such as did the user experience any tooth sensitivity. If the answer were "yes", the processor 62 could implement one or more changes in the operation or characteristics of the electric toothbrush to reduce tooth sensitivity (e.g., altering the speed, frequency, amplitude of the brush head movements or altering the bristle configuration). The memory 64 can store the instructions and data associated with the questions, answers, and algorithms for the sequence of questions. These instructions and data can be periodically updated if the oral-care system is connected to a network.

Some information that can be displayed on the display 45 that is not related to the characteristics of the electric toothbrush 35, or characteristics of the oral-care regimen, will now be described. A coupon code (or equivalent) that can be redeemed for a coupon or discount (either via the Internet or in store) can be provided at a variety of times during use of the electric toothbrush 35. For example, a coupon code might be displayed after a predetermined period of brushing or when a component, such as a toothbrush head, should be replaced. The coupon code can be displayed when multiple products from the same manufacturer are used or when certain characteristics of an oral-care regimen have been fulfilled (e.g., completion of a predetermined number of brushing cycles that have lasted for a minimum period of time, such as 2 minutes). Other information, such as weather, music, news, sports scores, stock quotes, etc., can be streamed to the oral-care system for display on the display 45

Figure 9:
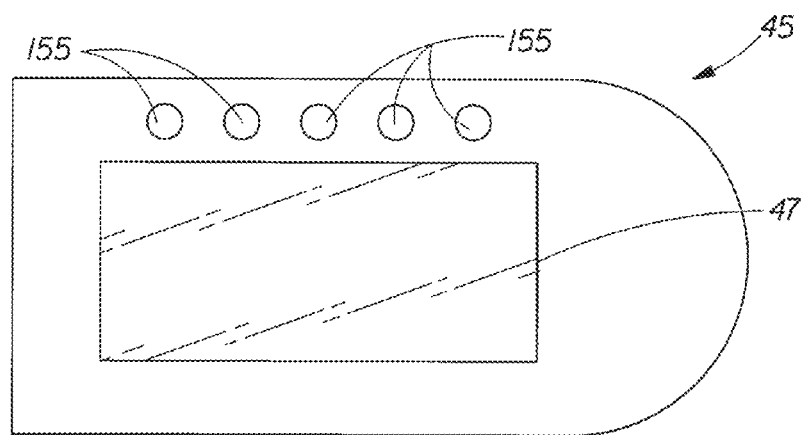
FIG. 9 is a front view of another embodiment of the display of FIG. 2, wherein the display comprises a plurality of light sources.

Referring to FIG. 9, in another embodiment, the display 45 and/or the sleeve 60 can incorporate one or more light sources 155 to illuminate the oral cavity. Examples of light sources include light emitting diodes, laser diodes, flash lamps, and any other light or electromagnetic energy source. The light sources can be arranged in a variety of patterns on either the display 45 and/or the sleeve 60, including in a line, along an edge of the display 45, or any combination thereof. A diffuser or lens can be placed over the one or more light sources 155 to diffuse or focus the light as desired. The diffuser or lens can be adjustable so that the intensity and/or the size/shape of the light pattern can be varied depending on user preference. In another embodiment, the light intensity can be varied by altering the voltage and/or current to the one or more light sources 155, to increase or decrease the intensity. The voltage and/or current can be varied by a switch, button, or dial located on the display 45 and/or sleeve 60 that is in electrical communication with the one or more light sources 155.

Figure 10:
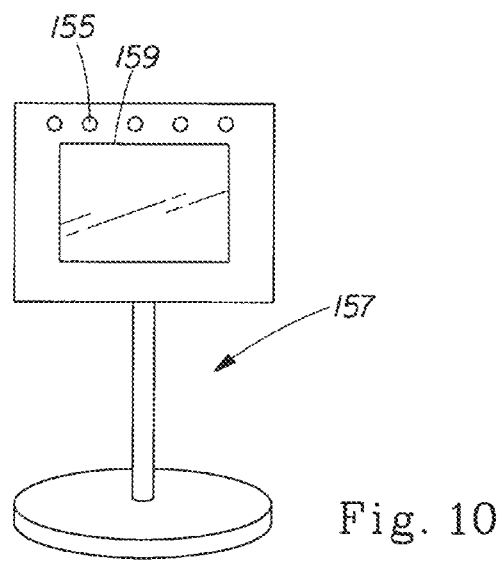
FIG. 10 is a perspective view of another embodiment of the present invention, illustrating a device comprising a mirror and a plurality of light sources.
Figure 11:
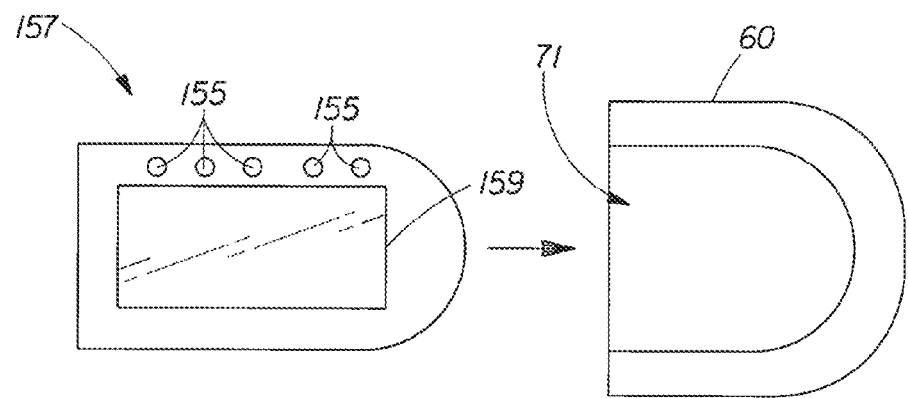
FIG. 11 is a front view of an alternate embodiment of the device of FIG. 10, wherein the mirror and light sources are sliding received within a mounting structure.

In another embodiment, the one or more light sources 155 may be disposed on a device 157 having a stand 158 but which does not include the screen 47, as shown in FIG. 10. In this embodiment, the screen 47 might be replaced by a mirror 159 so that the light sources 155 illuminate the oral cavity and the mirror 159 of the device 157 can be used to view the oral cavity.

The device 157 can be provided in a variety of shapes and sizes. The device 157 and/or or the one or more lights sources can be configured to rotate or swivel so that a user can direct the light from the light sources in a manner that best illuminates the oral cavity, including hard and soft tissue like the teeth and gums. In one embodiment, a plurality of mirrors can be provided, wherein one of the mirrors magnifies the reflections from the oral cavity to improve the detailed viewing thereof.

In one embodiment, the one or more light sources 155 of the display 45 or the device 157 can be used with an oral-care composition, such as a dentifrice or rinse, that comprises a disclosing agent or a plurality of disclosing agents. The disclosing agent can be utilized to provide visual indication of one or more conditions of the oral cavity to an observer and/or user. As used herein, the phrase "conditions of the oral cavity" is used to refer to dental plaque, tartar, debris, tooth decay, bio films, soft tissue abnormalities, soft tissue lesions, etc. within the oral cavity. As used herein, the terms "plaque" and "dental plaque" are used to refer to a biofilm that builds up on teeth, on gingival tissue, oral hard tissue, and/or oral soft tissue. "Plaque bacteria" means bacteria that causes plaque to form.

The visual indication of oral conditions to the observer and/or user can assist the observer and/or user in removal of the conditions or in identifying conditions which should be treated by a professional, e.g. dentist, oral surgeon, etc. The disclosing agents may visually indicate a condition within the oral cavity by providing a visual contrast between the conditions of the oral cavity and other tissues and surfaces within the oral cavity. For example, a disclosing agent may be selected such that when the disclosing agent is subjected to energy from an energy source, such as the light sources 155 of the display 45, the disclosing agent fluoresces at locations of the oral conditions. Other examples of providing visual contrast are discussed hereafter. As a specific example, the disclosing agent may be applied to the oral cavity and visually highlight and/or indicate remaining plaque to a user and/or observer.

In some embodiments, any agents, materials, elements, compounds, or compositions, which will absorb light energy at a first range of wavelengths and, in response, emit light at second range of wavelengths can be a suitable disclosing agent, so long as it is safe for use in the manner intended here. In some embodiments, the first range of wavelengths may be different than the second range of wavelengths. For example, the disclosing agent may comprise a fluorophore.

Some examples of suitable disclosing agents include fluoroscein, dibromofluoroscein, tribromofluoroscein, tetrabromofluoroscein, other fluorescein derivatives (including salts thereof), xanthenes, pyrenes, e.g. pyranine, D&C Blue No. 1, D&C Blue No. 2, D&C Green No. 3, D&C Red No. 3, D&C Red No. 6, D&C Red No. 7, D&C Red No. 21, D&C Red No. 22, D&C Red No. 27, D&C Red No. 28, D&C Red No. 33, D&C Red No. 40, D&C Yellow No. 5, D&C Yellow No. 6, D&C Yellow No. 10, combinations thereof or any other dye approved for use in drugs and cosmetics by regulatory agencies such as, for example, The United States Food and Drug Administration. Other suitable disclosing agents may include dyes sold under the trade name Alexafluor™ by Invitrogen Corporation located in Carlsbad, Calif.

In embodiments where the disclosing agent comprises a fluorophore, the disclosing agent may be selected such that the disclosing agent fluoresces in response to electromagnetic energy from the light sources 155 having wavelengths which range from about 380 nm to about 780 nm, or any individual number within the range. In some embodiments, the disclosing agent may fluoresce in response to electromagnetic energy having wavelengths which are greater than about 380 nm, greater than about 390 nm, greater than about 400 nm, greater than about 410 nm, greater than about 420 nm, greater than about 430 nm, greater than about 440 nm, greater than about 450 nm, greater than about 460 nm, greater than about 470 nm, greater than about 480 nm, greater than about 490 nm, greater than about 500 nm, greater than about 510 nm, greater than about 520 nm, greater than about 530 nm, greater than about 540 nm, greater than about 550 nm, greater than about 560 nm, greater than about 570 nm, greater than about 580 nm, greater than about 590 nm, greater than about 600 nm, greater than about 610 nm, greater than about 620 nm, greater than about 630 nm, greater than about 640 nm, greater than about 650 nm, greater than about 660 nm, greater than about 670 nm, greater than about 680 nm, greater than about 690 nm, greater than about 700 nm, greater than about 710 nm, greater than about 720 nm, greater than about 730 nm, greater than about 740 nm, greater than about 750 nm, greater than about 760 nm and/or less than about 780 nm, less than about 770 nm, less than about 760 nm, less than about 750 nm, less than about 740 nm, less than about 730 nm, less than about 720 nm, less than about 710 nm, less than about 700 nm, less than about 690 nm, less than about 680 nm, less than about 670 nm, less than about 660 nm, less than about 650 nm, less than about 640 nm, less than about 630 nm, less than about 620 nm, less than about 610 nm, less than about 600 nm, less than about 590 nm, less than about 580 nm, less than about 570 nm, less than about 560 nm, less than about 550 nm, less than about 540 nm, less than about 530 nm, less than about 520 nm, less than about 510 nm, less than about 500 nm, less than about 490 nm, less than about 480 nm, less than about 470 nm, less than about 460 nm, less than about 450 nm, less than about 440 nm, less than about 430 nm, less than about 420 nm, less than about 410 nm, or less than about 400 nm.

In some embodiments, the disclosing agent may fluoresce in response to electromagnetic energy from the light sources 155 having wavelengths which are from about 400 nm to about 530 nm. For example, in one specific embodiment, the disclosing agent fluoresces in response to electromagnetic energy having a wavelength of about 470 nm. In other embodiments, the disclosing agent may fluoresce in response to electromagnetic energy having wavelengths between about 400 nm to about 440 nm. In other embodiments, the disclosing agent may fluoresce in response to electromagnetic energy having wavelengths between about 440 nm to about 530 nm. Additionally, embodiments are contemplated where the disclosing agent fluoresces in response to electromagnetic energy having wavelengths which are outside of the visible light spectrum, e.g. either higher or lower, combinations of higher and lower, and/or combinations of higher, lower, and visible spectrum. For example, embodiments are contemplated where the disclosing agent fluoresces in response to ultraviolet light, e.g. UVA about 315 nm to about 400 nm; UVB about 280 nm to about 315 nm; and/or UVC less than about 280 nm.

In some embodiments, the disclosing agent may emit electromagnetic energy having wavelengths of greater than about 400 nm. For example, disclosing agent useful in the present invention may emit electromagnetic energy having wavelengths which are greater than about 410 nm, greater than about 420 nm, greater than about 430 nm, greater than about 440 nm, greater than about 450 nm, greater than about 460 nm, greater than about 470 nm, greater than about 480 nm, greater than about 490 nm, greater than about 500 nm, greater than about 510 nm, greater than about 520 nm, greater than about 530 nm, greater than about 540 nm, greater than about 550 nm, greater than about 560 nm, greater than about 570 nm, greater than about 580 nm, greater than about 590 nm, greater than about 600 nm, greater than about 610 nm, greater than about 620 nm, greater than about 630 nm, greater than about 640 nm, greater than about 650 nm, greater than about 660 nm, greater than about 670 nm, greater than about 680 nm, greater than about 690 nm, greater than about 700 nm, greater than about 710 nm, greater than about 720 nm, greater than about 730 nm, greater than about 740 nm, greater than about 750 nm, greater than about 760 nm and/or less than about 800 nm, less than about 780 nm, less than about 770 nm, less than about 760 nm, less than about 750 nm, less than about 740 nm, less than about 730 nm, less than about 720 nm, less than about 710 nm, less than about 700 nm, less than about 690 nm, less than about 680 nm, less than about 670 nm, less than about 660 nm, less than about 650 nm, less than about 640 nm, less than about 630 nm, less than about 620 nm, less than about 610 nm, less than about 600 nm, less than about 590 nm, less than about 580 nm, less than about 570 nm, less than about 560 nm, less than about 550 nm, less than about 540 nm, less than about 530 nm, less than about 520 nm, less than about 510 nm, less than about 500 nm, less than about 490 nm, less than about 480 nm, less than about 470 nm, less than about 460 nm, less than about 450 nm, less than about 440 nm, less than about 430 nm, less than about 420 nm, or less than about 410 nm.

Figure 12:
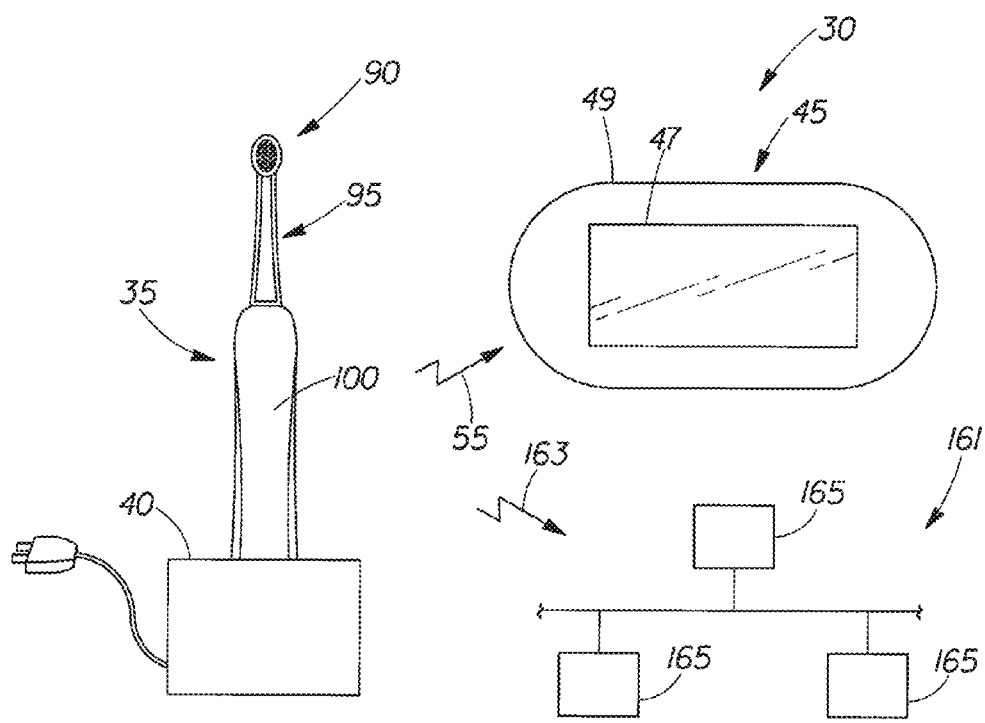
FIG. 12 is a schematic view of another embodiment of the present invention comprising an oral-care system that is linked to a network.

Referring to FIG. 12, the oral-care system 30 may further be adapted to communicate data between itself and a network 161, including local area networks (LANs), wide area networks (WANs), portions of the Internet such as a private Internet, a secure Internet, a value-added network, or a virtual private network. The oral-care system 30 can communicate with the network 161 by a data link 163, which can be a wireless or a signal line. Suitable network clients 165 may include personal computers, laptops, workstations, disconnectable mobile computers, mainframes, information appliances, personal digital assistants, and other handheld and/or embedded processing systems. The signal lines that support communications links to the network 161 and clients 165 may include twisted pair, coaxial, or optical fiber cables, telephone lines, satellites, microwave relays, modulated AC power lines, and other data transmission "wires" known to those of skill in the art. Further, signals may be transferred wirelessly through a wireless network or wireless LAN (WLAN) using any suitable wireless transmission protocol, such as the IEEE series of 802.11 standards. Although particular individual and network computer systems and components are shown, those of skill in the art will appreciate that the present invention also works with a variety of other networks and computers.

Figure 13:
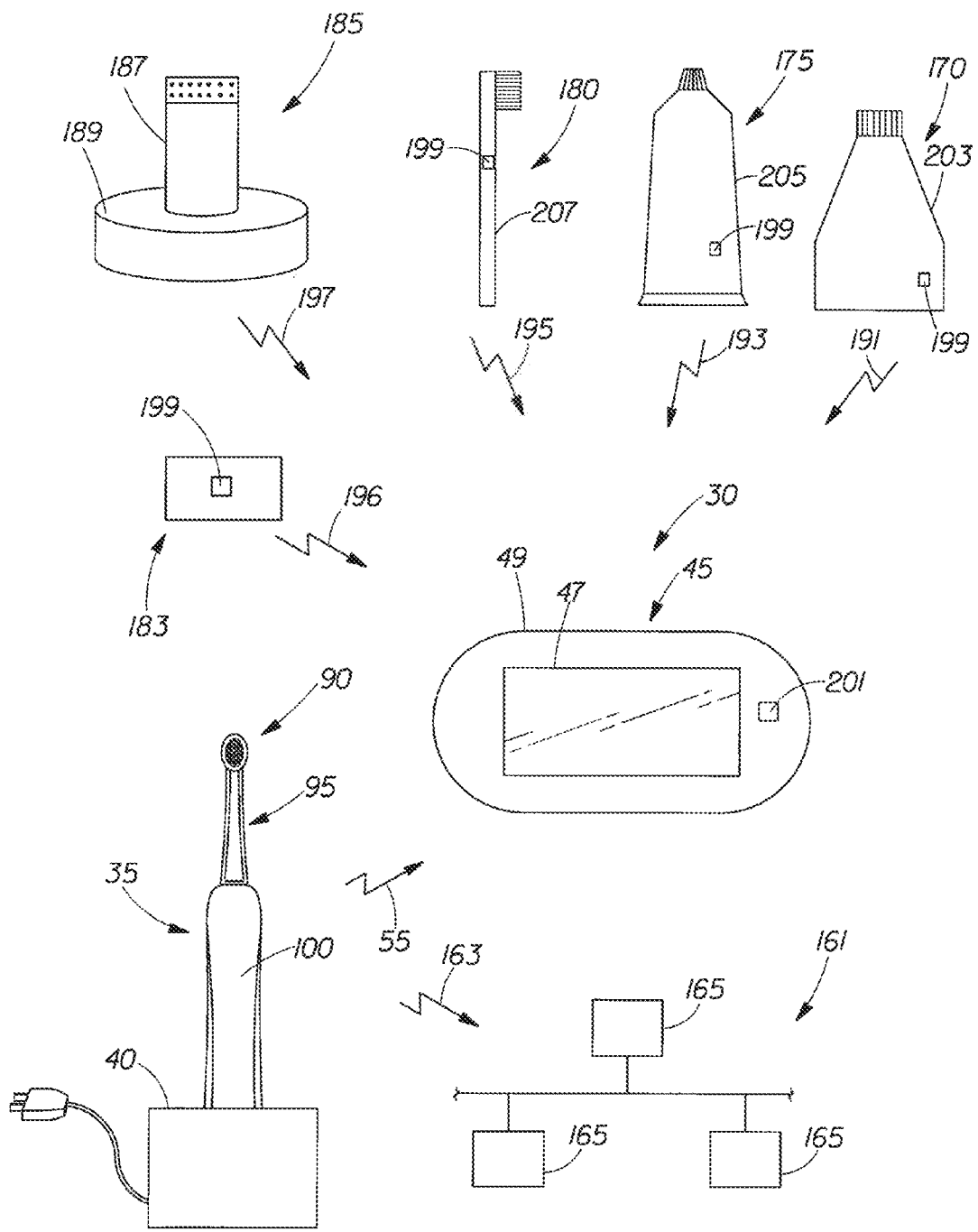
FIG. 13 is a schematic view of an alternate embodiment of the present invention comprising a plurality of personal-care products.

Referring to FIG. 13, the oral-care system 30, a plurality of oral-care products 170, 175, 180, and 183, and a non-oral-care personal care system 185 are illustrated. The oral-care product 170 is illustrated as a packaged oral-care rinse product; the oral-care product 175 is illustrated as a packaged dentifrice product, the oral-care product 180 is illustrated as a manual toothbrush product, the oral-care product 183 is illustrated as a packaged tooth whitening product (e.g., as disclosed in U.S. Pat. No. 5,891,453), and the personal care system 185 comprises an electric razor 187 that is received within a base 189. Examples of razors that are suitable for use with the present invention are disclosed in U.S. Pat. Nos. 6,594,904; 6,442,839; 6,298,559; 6,295,734; 6,237,232; 6,216,349; 6,212,777; 6,041,926; 5,787,586; 6,192,586; 6,185,822; 6,052,903; 6,889,438; 6,029,354; 6,161,287; 2006/0200992; 2005/198842; 2006/0080837; 2006/0032054; 2006/0032055; 2006/0037107; and 2006/0032053. The oral-care products 170, 175, 180, and 183 can communicate using data links 191, 193, 195, and 196, respectively, with the display 45. The personal care system 185 can communicate via data link 197 with the display 45. While certain products have been shown for ease of discussion, it will be understood that a variety of products and personal care systems can be substituted. The data links can be wireless or via signal lines as previously discussed. The personal care system 185 and products 170, 175, 180, 183 may also be connected to a network as previously described. As will be appreciated, the present invention is suitable for use with products that comprise an internal power supply as well as products that do not, such as a packaged rinse product.

As previously discussed, the products and systems of the present invention can use a variety of methods and devices to store, transmit and/or communicate data between the systems/products and the display. The term "data" is intended to refer to any digital or analog information in any form that is transferred or communicated between two devices or components. Data may include any data actively transmitted by a data transmitter and/or data that is passively detected by a data reader. Data may include ones and zeroes if the data that is communicated is digital. In another embodiment, data could be a series of digits, such as 12345678, wherein each digit could represent information about a characteristic of an oral-care device (e.g., for a manual toothbrush, the first digit could represent the brushing time in minutes, the second digit could represent the number of months until the brush should be replaced, the third and fourth digits could represent a type unique reward, etc.). Data may include the arrangement of optical elements (e.g., a bar code) that represent information. Data may include the presence or absence of electromagnetic energy (e.g., such as a magnetic field) and the like. The data may be interpreted or decoded by the processor 62. For instance, where the data is a series of digits, such as 12345678, the processor 62 and/or associated memory could comprise a set of instructions that would be able to decode or interpret the data to determine what information is represented by the data.

A data transmitter is a device or component that actively transmits data to a data reader. An RFID tag is an example of a data transmitter. A data communicator is a device or component that may or may not actively transmit data but which has data that is capable of being detected. While a data transmitter, such as an RFID tag, is a type of date communicator, a data communicator need not necessarily actively transmit data. Examples of data communicators that contain data that that may be detected or read by a data reader but which do not actively transmit data include a bar code (wherein the bar code reader is the data reader), a spotcode, a non-contact photo-electric sensor, or a hall effect magnet (wherein the hall effect sensor is the data reader). One example of this would be a magnet in the personal care device and a hall-effect sensor or reed switch as the data reader. Thus, as will be appreciated, the phrases "data communicators," "data transmitters," and "data readers" are intended to encompass a wide variety of devices and arrangements for the transmission, communication, and/or detection of a variety of analog or digital data, including the mere detection of the presence of a data communicator. Examples of such devices include, without limitation, optical devices, magnetic and electromagnetic devices, bar codes, or any other devices capable of providing data communication as described herein. The phrase "data communication" is intended to encompass all the methods and forms by which data may be transmitted, communicated, and/or detected by a devices of the present invention, including data readers, data transmitters, data communicators, as well as data communication between a two components such as a display and an electric toothbrush.

A data reader can be associated with an electric toothbrush in variety of ways. For example, the data reader can be provided in the toothbrush handle, a charging station, a detached display or other detached device, a toothbrush stand, etc. In one embodiment, a data transmitter can be provided as a radio frequency identification (RFID) tag that can be used to transmit data between the personal care product and the display 45. As known in the art, an RFID tag comprises an electronic chip that contains encoded information and an antenna that transmits and/or receives information or data (including information stored by the chip) using radio waves. A reader is used to decode the data transmitted from the RFID tag. The RFID tag may be provided without an internal power supply, and the minute electrical current induced in the antenna by the incoming radio frequency signal from the reader provides just enough power for the integrated circuit in the tag to power up and transmit a response to the reader. The RFID tag can be a read only tag or a read/write tag. The data stored by a read only tag is pre-programmed, typically by a manufacturer, in non-volatile memory and cannot be changed by a later user of the personal care product or system. The data stored by a read/write tag can be later rewritten to the tag during later use, typically by the reader.

The data stored by the RFID tag or other data transmitters/communicators can be quite varied, including any personal care information. Some of the categories of data includes product identification data (e.g., the brand name or product name) and product usage or regimen data (e.g., usage time, such as 1 minute regimen for a rinse, text or graphical instructions concerning product usage), one or more rewards, and component or product replacement data (e.g., number of times or length of time that a component or product can be used before it should be replaced). Instructional images, text, or data can be particularly useful for children in establishing appropriate brushing regimens. Data can be directly displayed on the display 45 or can be used as an input to the processor 62 (FIG. 4) for a function or feature of the display 45. For example, an RFID tag 199 for the rinse product 170 could store usage data that states the recommended usage time for the product is 1 minute. The RFID tag can transmit the usage data to a reader 201 associated with the display 45. The usage data can be used as an input for a count-up or count-down timer (e.g., 130 in FIG. 7) that is then set to one minute. To initiate the data transmission from the RFID tag 199 to the reader 201, the product containing the RFID tag 199 need only be placed in sufficient proximity to the reader 201 to power-up the RFID tag.

The RFID tag can be embedded within or attached to the packaging of a personal care product, such as the rinse bottle 203 or the dentifrice tube 205. The RFID tag 199 might also be attached to or embedded within the product itself where possible. For instance, the RFID tag might be embedded or attached to the handle 207 of the manual toothbrush 180.

The data communication between a data communicator and a data reader can occur at a variety time before, during, or after an oral-care regimen and can be sequential or modulated. For instance, each of a plurality of oral-care products having an RFID tag might be moved in proximity of the display 45 so that the RFID tag can transmit its data to a reader 201 that is part of the display 45, the sleeve 60, or another component of one of the personal care systems. The data transmission can occur prior to each usage of the oral-care product or may only need to occur once, such as the first time the product is used, and the data is thereafter stored by the reader 201 (or the memory 64) or a component associated with the reader 201. A counter can be implemented that stores the number of times that data is transmitted from the RFID tag to the reader 201 for each personal care product.

In one method of the present invention, the manual toothbrush 180 having an RFID tag 199 can be moved near the display 45 having the reader 201 to transmit identification, usage information, and replacement information to the reader 201. The identification data can comprise the name of the product, and the usage data can comprise the recommended usage time (e.g., 2 minutes per brushing cycle). The replacement data can comprise the number of times that the manual toothbrush can be used before it should be replaced. Replacement may be desirable if the bristles have degraded sufficiently to affect the cleaning performance of the toothbrush. The reader 201 reads the transmitted data and the display 45 displays the name of the product and initiates a 2 minute timer for a brushing regimen. Each time the manual toothbrush 180 transmits data to the reader 201, a counter implemented by the processor 62 increments by one. Once the counter reaches the value of the replacement data, the display 45 can display an image, text, or other signal that the manual toothbrush 180 (or any replaceable component of other products) should be replaced. If the display is in data communication with a computer network, a replacement product could automatically be ordered for the user. The manual toothbrush 180 might also be moved in reading proximity of the reader 201 at the end of the brushing cycle, wherein the second data transmission to the reader within a predetermined period of time (e.g., 5 minutes) can be used to indicate the termination of the brushing cycle by the user. The reader 201, or components associated therewith, can be programmed to analyze the start and stop points of a plurality of brushing cycles and to display helpful feedback to the user of the personal-care products and/or systems. For instance, average brushing times/dates might be displayed. The analytical data might be displayed at predetermined times according to a calendar function associated with display 45 (e.g., once a week). Next, the user might move the rinse package 203 near the display 45 to transmit its data to the reader 201 after which the display 45 could display the product identification data and initiate a timer for use of the rinse by the user. Likewise, the packaged tooth whitening product 183 can be moved near the display 45 to transmit its data to the reader 201 after which the display 45 could display the product identification date and initiate a timer for the length of use of the tooth whitening product by the user (e.g., 5, 10, 15, 20, 25, or 30 minutes). Reminders for future use of the packaged tooth whitening product 183, or other product, could also be displayed based upon a calendar function or analysis of the oral-care regimen data.

One or more of the personal-care products, displays, devices, and/or system components described herein can be bundled together for distribution to a user as a kit. For example, a packaged dentifrice product, a manual toothbrush product, and a packaged rinse product in combination with a display capable of communicating with each of these products can be provided as a kit.

Figure 14:
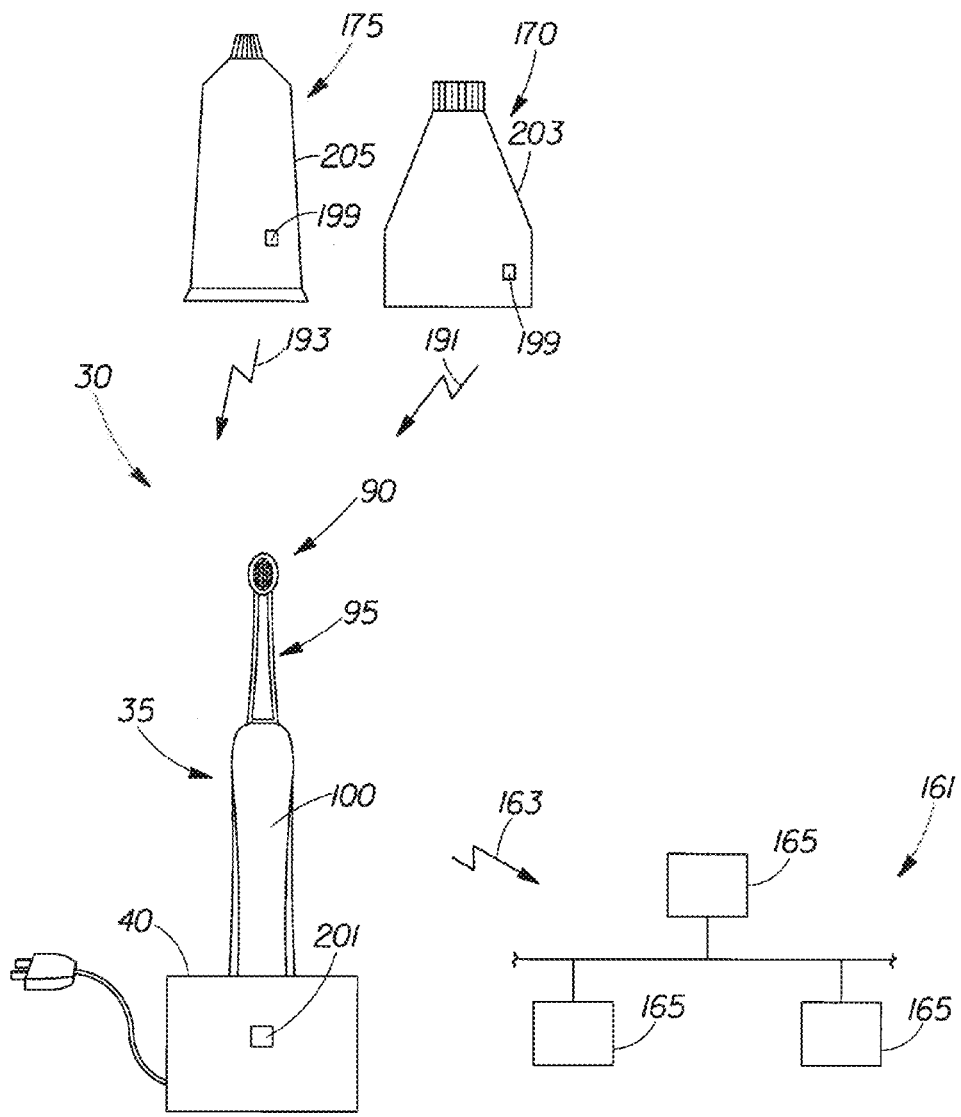
FIG. 14 is a schematic view of an alternate embodiment of the present invention comprising a plurality of personal-care products.

In another embodiment, one or more oral-care products can communicate directly with the electric toothbrush and/or its base. Referring to FIG. 14, a system 30 comprising a plurality of oral-care products 35, 170 and 175 is illustrated. The oral-care product 170 is illustrated as a packaged oral-care rinse product and the oral-care product 175 is illustrated as a packaged dentifrice product. The oral-care products 170 and 175 can communicate using data links 191 and 193 with the electric toothbrush 35 and/or its base 40. While certain products have been shown for ease of discussion, it will be understood that a variety of other products and personal care systems can be substituted. The data links can be wireless or via signal lines as previously discussed. The system 30 and products 35, 170, and 175 may also be connected to a network 161 via a data link 163, as previously described.

The system 30 can incorporate one or more of the electrical components previously described and illustrated in FIG. 4. In one embodiment, the electrical components are incorporated in the electric toothbrush 35 and/or the base 40. In another embodiment, the electrical components are incorporated in the handle 100 of the electric toothbrush 35. The oral-care products 170 and 175 can each incorporate one or more data communicators 199. The data communicators can be provided in any form, including but not limited to an RFID tag, a bar code, a shot code (e.g., an arrangement of black and white blocks which can be detected), or a magnet as previously described. A reader 201 may be located on the base 40, as shown in FIG. 14, or may be associated with the electric toothbrush 35. The reader 201 is capable of data communication with the data communicators 170 and 175. The data that may be transmitted by the data communicators and/or detected or received by the reader is varied and can be any of the information previously described.

In one example, the data communication includes data concerning the type of dentifrice or rinse that is part of the packaged products 170 and 175. With regard to the packaged dentifrice product 175, the data can include a code or description of the dentifrice or its ingredients, such as a sensitivity dentifrice, polishing dentifrice, light activated dentifrice, whitening dentifrice, etc. The data may be processed by the one or more processors 62 to determine, modify, change, implement, control, activate, initiate, and/or set one or more characteristics of the electric toothbrush 35. The characteristics of the electric toothbrush 35 can be quite varied and may include any of the characteristics previously described.

Figure 15:
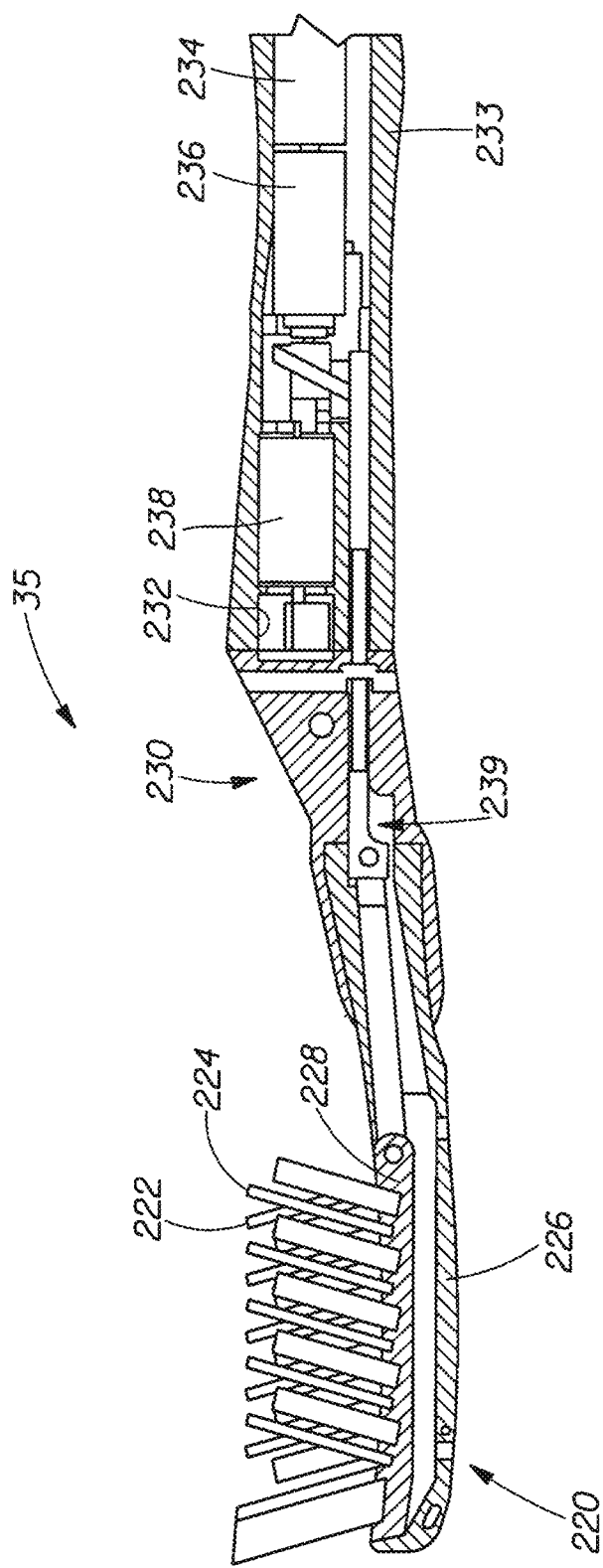
FIG. 15 is a cross-sectional side view of an electric toothbrush suitable for use with the present invention.
Figure 16:
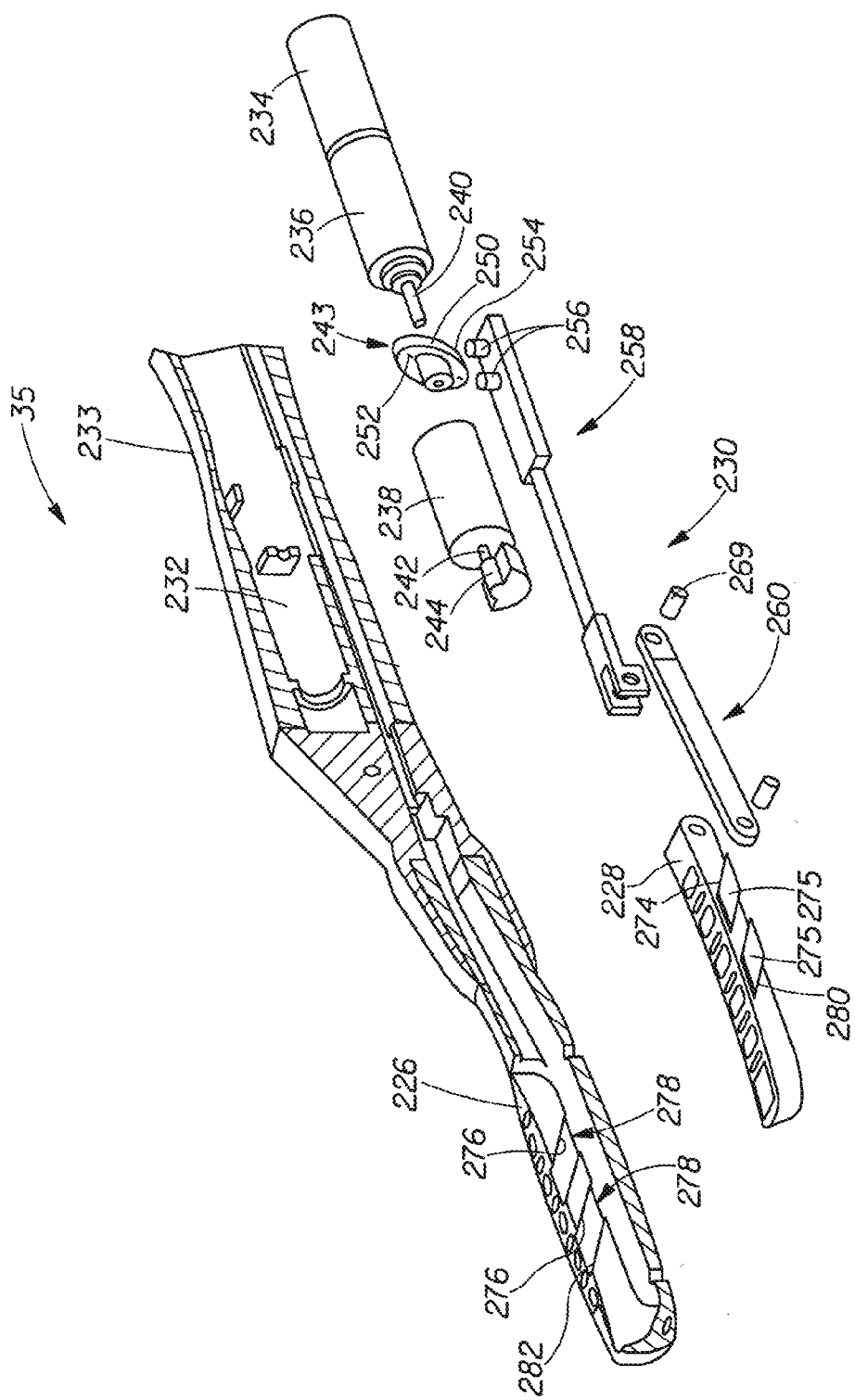
FIG. 16 is an exploded perspective view of the electric toothbrush of FIG. 15.

In one embodiment, the characteristic may include the bristle field configuration, which may be adapted or changed as a result of the processing of data communicated by the data transmitter to the reader, which is then communicated to the processor 62. Referring to FIGS. 15, 16, and 17, an electric toothbrush 35 is illustrated whose bristle field configuration may be changed as a result of processing data from a data transmitter or communicator. The toothbrush 35 comprises a head 220 and an outer bristle field 222 and an inner bristle field 224. Additional bristle fields may also be provided. The outer bristle field 222 may extend from a fixed component 226, and the inner bristle field 224 may extend from a movable component 228. In some embodiments, the auxiliary bristle field 226 may extend from the fixed component 226 and/or the movable component 228.

An actuator assembly 230 can be disposed within a cavity 232 of the handle 233 of the electric toothbrush 35. In some embodiments, the actuator assembly 230 includes a power source 234, a first motor 236, a second motor 238, and a drive system 239. The power source 234 is schematically depicted to include, for example, a battery such as a AA or AAA battery. The first motor 236 may include an electric motor powered by the battery and may include an output shaft 240 (shown in FIG. 16). The second motor 238 may include an electric motor, which may also be powered by the battery, having an output shaft 242 and an eccentric weight 244.

The drive system 230 may operably couple the first motor 236 to the movable component 228 of the head 220. The first motor 236 may operate as a conventional rotary motor to spin the output shaft 240 and drive the drive system 230. The second motor 238 may also include a conventional rotary motor; however, upon actuation, the eccentric weight 244, which is attached to the output shaft 242, may cause the toothbrush to vibrate similarly to the Oral-B Pulsar™ toothbrush that is commercially available from The Procter & Gamble Company and described in U.S. Pat. No. 6,564,416 and 2005/0235439. Additionally, embodiments are contemplated where a user may select between actuation of either or both of the motors 236, 238. In some embodiments, the motors 236, 238 may work in conjunction with each other, and/or independently of one another.

With continued reference to FIG. 15, as well as FIG. 16, the handle 234, the fixed component 226, and the movable component 228 may be separate components. These components may be formed separately and subsequently assembled. As mentioned above, the handle 234 may include a cavity 232 containing the actuator assembly 230. In the depicted form of the handle 234, the cavity 232 is complexly shaped to securely accommodate each of the components of the actuator assembly 230, as well as a portion of the fixed component 226 of the head 220. However, in an alternate form, the cavity 232 may be uniformly shaped and the components of the actuator assembly 230 may be fixed therein with an adhesive or some other device. In still another form, the fixed component 226 of the head 220 and handle 234 may be formed of a single piece or separate pieces.

During operation, the power source 234, for example a battery, may provide electrical energy to the first motor 236. The output shaft 240 of the first motor 236 may then effect a rotation of a drive cam 248. As the drive cam 248 rotates, a flange 250 rotates and the inclined surfaces 252, 254 continuously slidably engage bosses 256 on linear follower link 258. This sliding engagement converts the rotational motion of the first motor 236 into linear displacement of the linear follower link 258. The linear follower link 258 thus drives the articulation link 260 and finally, the movable component 228.

Referring to FIG. 17, the movable component 228 is illustrated in a first position, which defines a first configuration for the bristle field(s) of the head 220 of the toothbrush 35. In this position, the axially forward portion 262 of the flange 250 of the drive cam engages the bosses 256 on the linear follower link. So configured, the linear follower link 258 is disposed in its left-most position relative to the orientation of FIG. 17. Consequently, the articulation link 260 is disposed in its left-most position. Additionally, the movable component 228 of the head 220 is disposed in its left-most and upward-most position relative to the fixed component 226. So positioned, the outer bristle field 222 and the inner bristle field 224 are generally aligned in height. Said another way, the outer bristle field 222 terminates at a first plane, which is identified by reference numeral 266 in FIG. 17, while the inner bristle field 224 terminates at a second plane, which is identified by reference numeral 268 in FIG. 17. In the first configuration, the first and second planes 266, 268 are generally the same plane. Thus, FIG. 18 depicts the bristles of the toothbrush 35 including the outer bristle field 222 and the inner bristle field 224 defining a first configuration of the head 220.

In this first configuration, the outer bristle field 222 is adapted to perform a first cleaning operation, while the inner bristle field 224 is adapted to perform a second cleaning operation. The first and second cleaning operations may generally identical, but direction dependent, or may not be generally identical. The first and second cleaning operations may include a surface cleaning operation, as well as an interproximal cleaning operation.

As the first motor 236 rotates the drive cam 248 to the second position indicated in FIG. 18, which defines a second configuration for the head 220 of the toothbrush 35, the axially rearward portion 284 of the flange 250 becomes disposed between the bosses 256 on the linear follower link 258. So configured, the linear follower link 258 is disposed in its right-most position, relative to the orientation of FIG. 17. Consequently, the articulation link 260 is disposed in its right-most position. Finally, the movable component 228 of the head 220 is disposed in its right-most and downward-most position relative to the fixed component 226. In this second position, the outer bristle field 222 extends a predetermined distance beyond the inner bristle field 224. Said another way, while the outer bristle field 222 still terminates at the first plane 266, the inner bristle field 224 terminates at the plane 268. The plane 268 is generally parallel to and offset below the plane 266. In one form, the plane 268 is disposed approximately between about 0 to about 10 millimeters below the plane 266 or any individual number within the range. Thus, FIG. 18 depicts the bristles of the toothbrush 35 including the outer bristle field 222 and the inner bristle field 224 defining a second configuration of the head 220.

Therefore, it should be appreciated that as the first motor 236 rotates the drive cam 248, the drive cam 248 displaces the linear follower link 258, which in turn displaces the articulation link 260 and the movable component 228, in some embodiments. More specifically, as the drive cam 248 displaces the linear follower link 258 from the first position illustrated in FIG. 17 to the second position illustrated in FIG. 18, for example, the linear follower link 258 pulls the articulation link 260 and causes it to slightly rotate in the counterclockwise direction about pin 269. Additionally, in some embodiments, as the articulation link 260 pulls the movable component 228 from the first position illustrated in FIG. 17 to the second position illustrated in FIG. 18, the rearward surfaces 274 of the bosses 275 on the movable component 228 (see FIG. 16) slidably displace along the rearward surfaces 276 of the slots 278 in the fixed component 226. Accordingly, the opposite occurs when the drive cam 248 displaces the movable component 228 from the second position illustrated in FIG. 18 to the first position illustrated in FIG. 17. Specifically, as the drive cam 248 displaces the linear follower link 258 from the second position illustrated in FIG. 18 to the first position illustrated in FIG. 17, the linear follower link 258 may push the articulation link 260 and cause it to slightly rotate in the clockwise direction about pin 269. Additionally, as the articulation link 260 pushes the movable component 228 between the second position illustrated in FIG. 18 to the first position illustrated in FIG. 17, the forward surfaces 280 of the bosses 275 on the movable component 228 may slidably displace along the forward surfaces 282 of the slots 278 in the fixed component 226. Thus, during use, the actuator assembly 230 may displace the inner bristle field 224 between two heights and longitudinal positions relative to the outer bristle field 222 thereby defining the two configurations of the head 220 discussed above.

The actuation of the first motor 236 to move the movable component 228 between the first and second positions may be controlled by the processor 62 as a result of the analysis of the data communicated between the reader 201 and the data communicators 199. In other embodiments, the processor 62 may control, including variable control, the speed, frequency, and/or amplitude of one or more bristle carriers or bristle fields as a result of the analysis of data communicated between the reader 201 and the data communicators 199. For example, the processor 62 may control operation of the motor 234 to move the movable component 228 to the bristle configuration shown in FIG. 18 (a first configuration) when the data communicated to the processor 62 indicates, or has been analyzed to indicate that, the packaged dentifrice product 175 may provide a sensitivity benefit to a consumer. The bristle configuration shown in FIG. 18 may be configured to provide a sensitivity benefit, such as fewer bristles contacting the teeth resulting in a less aggressive tooth and gum feel, such that the first configuration provides the same, similar, and/or synergistic benefit with the dentifrice. The sensitivity benefit of the dentifrice may be provided by one or more ingredients or agents. An example of some ingredients which may be suitable is described in USPN 2002/0041852. The sensitivity benefit may be identified to the consumer by one or more images, phrases, or slogans associated with the packaged dentifrice product 175. The data that is communicated to the processor 62 may include an identifier that that the dentifrice has a sensitivity benefit or an identifier for one or more of the ingredients or agents of the dentifrice. In addition or alternatively, the processor 62 might control the operation of motor 238 so that the motor rotates at a speed that delivers a less aggressive movement or vibration (frequency and/or amplitude) to the head 220 and the bristles thereof. Other benefits that may be delivered by a dentifrice product, or other oral-care product, and which may have data, such as an identifier, that is communicated to the processor 62 include, whitening, polishing, malodor, anti-gingivitis, anti-cavity, anti-tartar, anti-erosion, and anti-plaque benefits as well as combinations thereof. The data that is communicated to the processor 62 from the dentifrice product 175 may identify one or more ingredients, agents or actives of the dentifrice, including but not limited to any of those described in U.S. Pat. Nos. 6,846,478; 6,740,311; 6,696,045; 2004/0126335; 2006/0171907; and 2003/0124065.

While some examples of embodiments of the present invention have been illustrated and described, it would be obvious to those skilled in the art that various other changes and modifications can be made without departing from the spirit and scope of the invention. Further features, application possibilities, and advantages, of the present invention may become apparent from the above description of embodiments of the invention and/or from the Figures of the accompanying drawings. It will be understood that any features described herein and/or represented by illustration, whether used singularly or in any combination, form the subject-matter of the present invention. It is therefore intended to cover in the appended claims all such changes and modifications that are within the scope of this invention.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care system, comprising:
    an electric toothbrush;
    a base for receiving the electric toothbrush, wherein the base includes a charger used for recharging a power source located within the electric toothbrush; and
    a display in continuous wireless data communication with the toothbrush during a brushing cycle wherein the brushing cycle expires at the end of a time period or when brushing of the last section of an oral cavity is complete;
    wherein the display is separate from the electric toothbrush and the base;
    wherein the display is structured to display information associated with a plurality of functional characteristics of an oral care regimen;
    wherein the display displays a schematic image of four or more segments of a user's dentition and a count-up or count-down timer for displaying the amount of time remaining in the brushing cycle, such that at various periods of time during the brushing cycle, the display signals the user to change the segment of the dentition that the user is brushing until brushing of the last segment of the user's dentition is complete and a reward is automatically displayed on the display to indicate successful completion of the brushing cycle;

wherein the display comprises buttons or switches to provide data input to the display and the display is arranged such that the data input can control functions or operations of the electric toothbrush.

2. The oral care system of claim 1, wherein the data communication is continuous during a brushing cycle.

3. The oral care system of claim 1, wherein the data communication is intermittent during a brushing cycle.

4. The oral care system of claim 1, wherein the display displays a reward after a timer has expired.

5. The oral care system of claim 1, wherein the display can further display information selected from the group consisting of coupon codes, weather, news, sports scores, stock quotes and music.

6. The oral care system of claim 1, wherein the display includes a user interface in the form of a touch screen.

7. The oral care system of claim 1, wherein the display includes a user interface in the form of buttons.

8. An oral care system, comprising:

an electric toothbrush;

a base for receiving the electric toothbrush, wherein the base includes a charger used for recharging a power source located within the electric toothbrush; and a display in continuous wireless data communication with the toothbrush during a brushing cycle wherein the brushing cycle expires at the end of a time period or when brushing of the last section of an oral cavity is complete;

wherein the display is separate from the electric toothbrush and the base;

wherein the display is structured to display information associated with a plurality of functional characteristics of an oral care regimen;

wherein the display displays a schematic image of four or more segments of a user's dentition and a count-up or count-down timer for displaying the amount of time remaining in the brushing cycle, such that at various periods of time during the brushing cycle, the display signals the user to change the segment of the dentition that the user is brushing until brushing of the last segment of the user's dentition is complete and a reward is automatically displayed on the display to indicate successful completion of the brushing cycle;

wherein the display incorporates a touch screen to provide data input to the display and the display is arranged such that the data input can control functions or operations of the electric toothbrush.

9. The oral care system of claim 8, wherein the data communication is continuous during a brushing cycle.

10. The oral care system of claim 8, wherein the data communication is intermittent during a brushing cycle.

11. The oral care system of claim 8, wherein the display displays a reward after a timer has expired.

12. The oral care system of claim 8, wherein the display can further display information selected from the group consisting of coupon codes, weather, news, sports scores, stock quotes and music.

13. The oral care system of claim 8, wherein the display includes a user interface in the form of a touch screen.

14. The oral care system of claim 8, wherein the display includes a user interface in the form of buttons.

* * * * *